United States Patent
Sato et al.

(10) Patent No.: US 11,234,639 B2
(45) Date of Patent: *Feb. 1, 2022

(54) CONTROLLER, TEMPERATURE SENSATION PROVIDING APPARATUS, TEMPERATURE SENSATION PROVIDING SYSTEM, CONTROL METHOD, AND STORAGE MEDIUM

(71) Applicant: ALPS ALPINE CO., LTD., Tokyo (JP)

(72) Inventors: Kunio Sato, Miyagi (JP); Toshihiko Saito, Miyagi (JP); Hajime Shikata, Miyagi (JP); Katsunari Sato, Nara (JP)

(73) Assignee: ALPS ALPINE CO., LTD., Tokyo (JP)

( * ) Notice: Subject to any disclaimer, the term of this patent is extended or adjusted under 35 U.S.C. 154(b) by 421 days.

This patent is subject to a terminal disclaimer.

(21) Appl. No.: 16/394,324

(22) Filed: Apr. 25, 2019

(65) Prior Publication Data

US 2019/0336064 A1 Nov. 7, 2019

(30) Foreign Application Priority Data

May 1, 2018 (JP) .............................. JP2018-088105

(51) Int. Cl.
*A61B 5/00* (2006.01)
*G05D 23/19* (2006.01)

(52) U.S. Cl.
CPC ......... *A61B 5/483* (2013.01); *G05D 23/1917* (2013.01)

(58) Field of Classification Search
CPC ..... G05D 23/20; G05D 23/1917; A61B 5/483
See application file for complete search history.

(56) References Cited

U.S. PATENT DOCUMENTS

| 10,884,440 | B2* | 1/2021 | Sato | G05D 23/1927 |
| 2005/0149153 | A1* | 7/2005 | Nakase | A61F 7/02 607/108 |
| 2006/0274041 | A1* | 12/2006 | Han | G06F 3/03543 345/163 |
| 2015/0007583 | A1* | 1/2015 | Murata | B60L 50/16 62/3.2 |

(Continued)

FOREIGN PATENT DOCUMENTS

| JP | 2001-166676 | 6/2001 |
| JP | 2017-146830 | 8/2017 |

OTHER PUBLICATIONS

Office Action dated Sep. 4, 2020 issued to related U.S. Appl. No. 16/380,022.

*Primary Examiner* — Natalie Huls
*Assistant Examiner* — Cynthia L. Davis
(74) *Attorney, Agent, or Firm* — IPUSA, PLLC (57) ABSTRACT

A controller controls a temperature sensation provider that provides temperature sensations to an object contacting a contact surface of the temperature sensation provider. The controller includes a database including control information that associates values of a temperature of the contact surface with values of a controlled variable of the temperature sensation provider for each of the temperature sensations, and a temperature controller that controls the temperature sensation provider based on a measured temperature of the contact surface, a temperature sensation to be provided, and the control information.

13 Claims, 4 Drawing Sheets

(56) References Cited

U.S. PATENT DOCUMENTS

| | | |
|---|---|---|
| 2017/0212589 A1 | 7/2017 | Domenikos et al. |
| 2018/0039331 A1* | 2/2018 | Warren .................. G06F 3/043 |
| 2018/0267609 A1 | 9/2018 | Strese et al. |
| 2019/0168612 A1* | 6/2019 | Schnur ................ G06F 3/03547 |
| 2019/0250710 A1* | 8/2019 | Yi ......................... A63F 13/285 |
| 2020/0355410 A1* | 11/2020 | Gruenwald ............. H01L 35/34 |

* cited by examiner

CONTROLLER, TEMPERATURE SENSATION PROVIDING APPARATUS, TEMPERATURE SENSATION PROVIDING SYSTEM, CONTROL METHOD, AND STORAGE MEDIUM

CROSS-REFERENCE TO RELATED APPLICATION

The present application is based upon and claims priority to Japanese Patent Application No. 2018-088105, filed on May 1, 2018, the entire contents of which are incorporated herein by reference.

BACKGROUND OF THE INVENTION

1. Field of the Invention

An aspect of this disclosure relates to a controller, a temperature sensation providing apparatus, a temperature sensation providing system, a control method, and a storage medium.

2. Description of the Related Art

There exists a known technology that can provide a temperature sensation (cold sensation or warm sensation) to an object (e.g., a finger) contacting a contact surface of a temperature sensation provider (e.g., a Peltier element) by driving the temperature sensation provider.

For example, Japanese Laid-Open Patent Publication No. 2001-166676 discloses a technology that enables a tactile sensation providing mechanism, which provides a tactile sensation to a finger by pressing a palmar surface of the finger with a tactile sensation providing part, to provide a temperature sensation. In this technology, a heating element or a heat-absorbing element (e.g., a Peltier element) is provided and positioned in the tactile sensation providing mechanism to contact a surface of a finger.

However, there is a case where a user does not feel an intended temperature sensation even if the temperature of a contact surface is controlled to a specific temperature to provide the intended temperature sensation. For example, there is a case where a user does not readily feel a temperature of 22° C. in a low temperature environment even if the temperature of a contact surface is controlled at 22° C. to provide the user with a temperature sensation of 22° C. That is, related-art temperature sensation providing apparatuses are susceptible to environmental temperatures.

SUMMARY OF THE INVENTION

In an aspect of this disclosure, there is provided a controller for controlling a temperature sensation provider that provides temperature sensations to an object contacting a contact surface of the temperature sensation provider. The controller includes a database including control information that associates values of a temperature of the contact surface with values of a controlled variable of the temperature sensation provider for each of the temperature sensations, and a temperature controller that controls the temperature sensation provider based on a measured temperature of the contact surface, a temperature sensation to be provided, and the control information.

DESCRIPTION OF THE PREFERRED EMBODIMENTS

The inventors of the present invention conducted a study to find out causes why related-art temperature sensation providing apparatuses are susceptible to environmental temperatures. The results of the study indicate, for example, that the temperature of a finger when using a temperature sensation providing apparatus varies, and that the user becomes sensitive or insensitive to a temperature sensation depending on the temperature of the finger. For example, there is a case where the temperature of a finger in a warm area is about 32° C. while the temperature of a finger is about 27° C. in a cold area. When a temperature of 22° C. is provided by a Peltier element, a finger with a temperature of about 32° C. can feel the temperature of about 22° C., but a finger with a temperature of about 27° C. cannot readily feel the temperature of about 22° C. because the difference between the temperatures of 22° C. and 27° C. is small. Based on these findings, the inventors further conducted a study to reduce the influence of environmental temperatures. The results of this study indicate that when providing a temperature that makes a finger insensitive, it is effective to provide a stronger temperature sensation.

Embodiments of the present invention are described below with reference to the accompanying drawings. Throughout the specification and the drawings, the same reference number is assigned to components having substantially the same function and configuration, and repeated description of those components is omitted.

<Configuration of Temperature Sensation Providing System>

Figure 1:
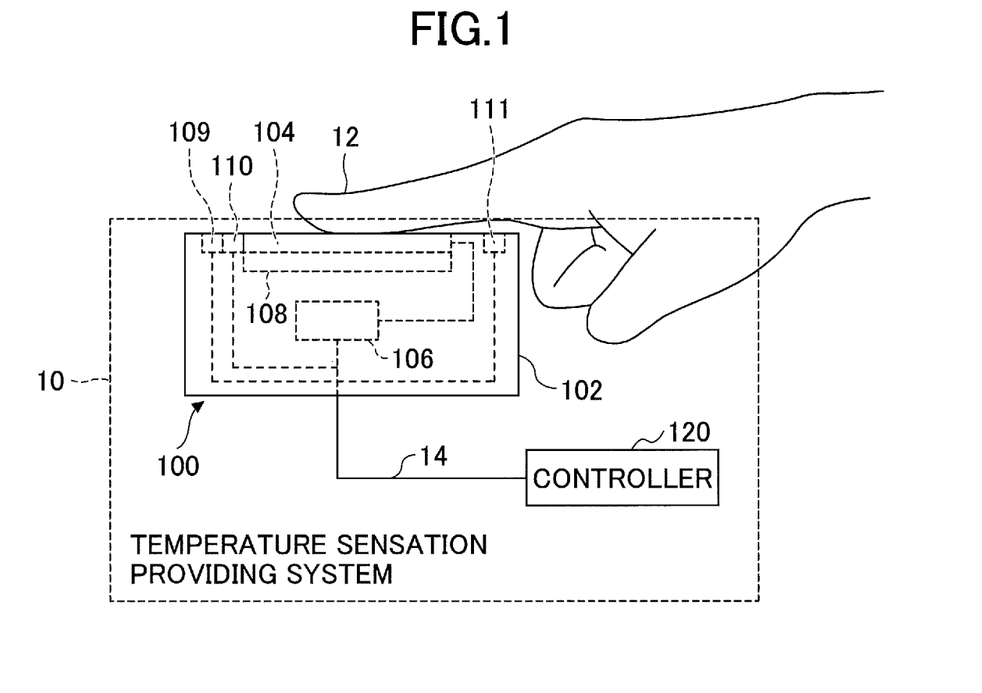
FIG. 1 is a drawing illustrating a configuration of a temperature sensation providing system according to an embodiment.

FIG. 1 is a drawing illustrating a configuration of a temperature sensation providing system 10 according to an embodiment. The temperature sensation providing system 10 can provide a cold sensation or a warm sensation to a finger 12 of a user that is in contact with a Peltier element 104 included in a temperature sensation providing apparatus 100. As illustrated in FIG. 1, the temperature sensation providing system 10 includes the temperature sensation providing apparatus 100 and a controller 120. The temperature sensation providing apparatus 100 and the controller 120 are connected to each other via a communication cable 14. In the descriptions below, for descriptive purposes, it is assumed that the temperature sensation providing system 10 provides a cold sensation. However, the temperature sensation providing system 10 may be configured to provide a warm sensation. That is, the temperature sensation providing system 10 is not limited to a cold sensation providing system.

The temperature sensation providing apparatus 100 is fixed to the finger 12 with a fixing part (e.g., a rubber belt) such that the finger 12 contacts a cooling surface of the Peltier element 104. The temperature sensation providing apparatus 100 includes a case 102, the Peltier element 104, a driver circuit 106, a heat sink 108, a contact sensor 109, a thermometer 110, and a heater 111.

The case 102 holds and houses other components. In the present embodiment, the case 102 has a cuboid shape. The case 102 is made of a comparatively hard material (e.g., a resin or a metal).

The Peltier element 104 is disposed such that a cooling surface (an example of a "contact surface") of the Peltier element 104 is exposed through a surface of the case 102. The Peltier element 104 is an example of a "temperature sensation provider". A surface of the Peltier element 104 located opposite the cooling surface is a radiation surface. When a driving current is supplied from the driver circuit 106, the cooling surface of the Peltier element 104 is cooled and the radiation surface radiates heat due to the Peltier effect. With this configuration, the Peltier element 104 can provide a cold sensation to the finger 12 contacting the cooling surface.

The driver circuit 106 is disposed in the case 102. The driver circuit 106 controls the Peltier element 104 by supplying a driving current to the Peltier element 104 according to a control signal supplied from the controller 120.

The heat sink 108 is a flat-plate shaped component that is disposed in close contact with the radiation surface of the Peltier element 104. The heat sink 108 is provided to release heat, which is generated on the radiation surface of the Peltier element 104 when the cooling surface of the Peltier element 104 is cooled, outside of the temperature sensation providing apparatus 100 (i.e., to the atmosphere). The heat sink 108 is made of a material (e.g., aluminum) with a comparatively-high heat radiation property. Also, the case 102 may be formed of a material (e.g., aluminum) with a comparatively-high heat radiation property, and the Peltier element 104 may be disposed to closely contact the case 102 so that the case 102 functions as a heat sink. In this case, the heat sink 108 of the temperature sensation providing apparatus 100 may be omitted.

The contact sensor 109 detects contact of the finger 12 with the Peltier element 104 and outputs information indicating the contact to the controller 120 via the communication cable 14. The contact sensor 109 is, for example, an electrostatic sensor capable of detecting a change in capacitance of the Peltier element 104 or a temperature sensor capable of detecting a change in temperature of the Peltier element 104.

The thermometer 110 measures the temperature of the cooling surface of the Peltier element 104 and outputs the measured temperature to the controller 120. The heater 111 heats the cooling surface of the Peltier element 104 under the control of the controller 120.

The controller 120 is provided outside of the temperature sensation providing apparatus 100 and controls the operation of the Peltier element 104 included in the temperature sensation providing apparatus 100. Specifically, the controller 120 supplies a control signal to the driver circuit 106 of the temperature sensation providing apparatus 100. In response, the driver circuit 106 provides a driving current to the Peltier element 104 and causes the Peltier element 104 to operate. The controller 120 may be implemented by a dedicated device or a general-purpose information processing apparatus (e.g., a smartphone or a personal computer). The controller 120 may be configured to supply a control signal to the driver circuit 106 of the temperature sensation providing apparatus 100 via wireless communication (e.g., Bluetooth (registered trademark), Wi-Fi, or near field communication (NFC)) instead of wired communication.

<Functional Configuration of Controller>

Figure 2:
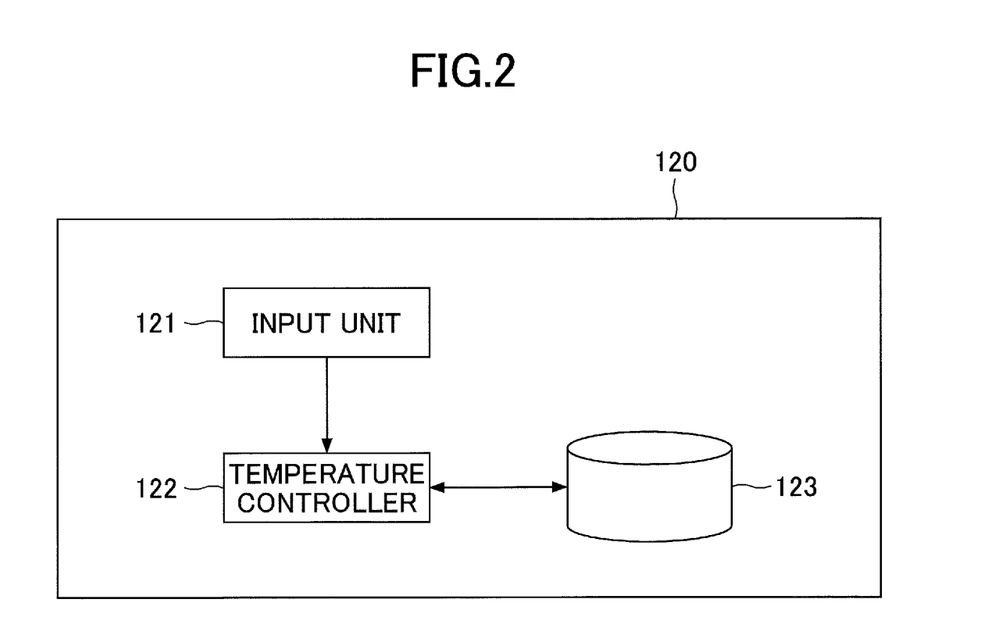
FIG. 2 is a drawing illustrating a functional configuration of a controller included in the temperature sensation providing system according to the embodiment.

FIG. 2 is a drawing illustrating a functional configuration of the controller 120 included in the temperature sensation providing system 10. As illustrated in FIG. 2, the controller 120 includes an input unit 121, a temperature controller 122, and a database 123.

The input unit 121 inputs information indicating a temperature to be provided by the temperature sensation providing apparatus 100. The information may be input by a user or may be input, in synchronization with an image, by a virtual reality (VR) display apparatus that functions together with the temperature sensation providing apparatus 100. For example, when the VR display apparatus displays an image of a person holding a cup containing a liquid and having a specific temperature (e.g., 22° C.), the VR display apparatus may input the specific temperature.

The database 123 stores control information that associates temperatures of the cooling surface of the Peltier element 104 with values of a controlled variable of the temperature sensation providing apparatus 100 for each temperature sensation. Table 1 below indicates an example of control information.

TABLE 1

| Target Temperature $T1$ | Cooling Surface Temperature $T21$ | $\Delta T_0$ (=T1-T21) | Temperature increment $\Delta T$ | Reached Temperature $T22$ |
|---|---|---|---|---|
| 20° C. | 32° C. | −12° C. | −12° C. | 20° C. |
|  | 28° C. | −8° C. | −9° C. | 19° C. |
|  | 25° C. | −5° C. | −7° C. | 18° C. |
| 22° C. | 32° C. | −10° C. | −10° C. | 22° C. |
|  | 28° C. | −6° C. | −7° C. | 21° C. |
|  | 25° C. | −3° C. | −5° C. | 20° C. |

In the example of Table 1, for each target temperature T1, cooling surface temperatures T21 of the cooling surface in contact with the finger 12 are associated with temperature increments ΔT at a predetermined time t1. The predetermined time t1 is, for example, within a range between 0.3 sec. and 1.0 sec. Here, the cooling surface temperature T21 of the cooling surface in contact with the finger 12 does not indicate the temperature of the cooling surface at the moment when the finger 12 touches the cooling surface, but indicates the temperature of the cooling surface in contact with the finger 12 at a time when the controller 120 starts a control process. Accordingly, the cooling surface temperature T21 depends not only on the environmental temperature of the Peltier element 104, but also on the temperature of the finger 12. In the example of Table 1, for the target temperature T1 of 22° C., the cooling surface temperature T21 of 32° C. is associated with the temperature increment ΔT of −10° C., the cooling surface temperature T21 of 28° C. is associated with the temperature increment ΔT of −7° C., and the cooling surface temperature T21 of 25° C. is associated with the temperature increment ΔT of −5° C. That is, when the cooling surface temperature T21 is 32° C., the actual temperature difference $\Delta T_0$ (=T1−T21) between the target temperature T1 and the cooling surface temperature T21 is −10° C., and the temperature increment ΔT is also −10° C. When the cooling surface temperature T21 is 28° C., the actual temperature difference $\Delta T_0$ is −6° C., but the temperature increment ΔT is −7° C. When the cooling surface temperature T21 is 25 t, the actual temperature difference $\Delta T_0$ is −3° C., but the temperature increment ΔT is −5° C. The actual temperature difference $\Delta T_0$ is an example of a "first temperature difference", and the temperature increment $\Delta T$ is an example of a "second temperature difference".

Thus, the control information is configured such that as the absolute value ($|\Delta T_0|$) of the actual temperature difference $\Delta T_0$ between the cooling surface temperature T21 and the target temperature T1 becomes smaller, the temperature increment $\Delta T$ associated with the cooling surface temperature T21 as a controlled variable deviates further from the actual temperature difference $\Delta T_0$. That is, in the control information, the deviation of the temperature increment $\Delta T$ at the predetermined time t1 from the actual temperature difference $\Delta T_0$ tends to become greater as the absolute value ($|\Delta T_0|$) of the actual temperature difference $\Delta T_0$ becomes smaller. This tendency need not be present in all actual temperature differences $\Delta T_0$, and is preferably present in the absolute values ($|\Delta T_0|$) of actual temperature differences $\Delta T_0$ that are less than or equal to a given value and at which the user tends to become insensitive. For the target temperature T1 of 20° C., cooling surface temperatures T21 are associated with temperature increments $\Delta T$ in a similar manner. The target temperature T1 is an example of a "temperature sensation" provided by the temperature sensation providing apparatus 100, and the temperature increment $\Delta T$ is an example of a "controlled variable". The database 123 preferably includes a greater number of target temperatures T1, and each of the target temperatures T1 is preferably associated with a greater number of combinations of cooling surface temperatures T21 and temperature increments $\Delta T$. The database 123 may also include information indicating driving currents corresponding to the temperature increments $\Delta T$.

The temperature controller 122 controls the operation of the Peltier element 104 of the temperature sensation providing apparatus 100 by supplying a control signal to the driver circuit 106 of the temperature sensation providing apparatus 100 based on control information stored in the database 123.

For example, the temperature controller 122 can drive the Peltier element 104 such that the temperature of the cooling surface of the Peltier element 104 becomes a target temperature by supplying a control signal to the driver circuit 106. More specifically, the temperature controller 122 can lower the temperature of the cooling surface of the Peltier element 104 by driving the Peltier element 104 with a higher driving current.

The above-described functions of the controller 120 are implemented by, for example, executing programs stored in a memory (e.g., a read-only memory (ROM) or a random access memory (RAM)) by a central processing unit (CPU) (which is an example of a "computer") of the controller 120. The programs executed by the CPU may be pre-installed in the controller 120 or may be obtained from an external source and installed into the controller 120. In the latter case, the programs may be provided via an external storage medium (e.g., a USB memory, a memory card, or a CD-ROM) or may be downloaded from a server on a network (e.g., the Internet).

<Control Process>

Figure 3:
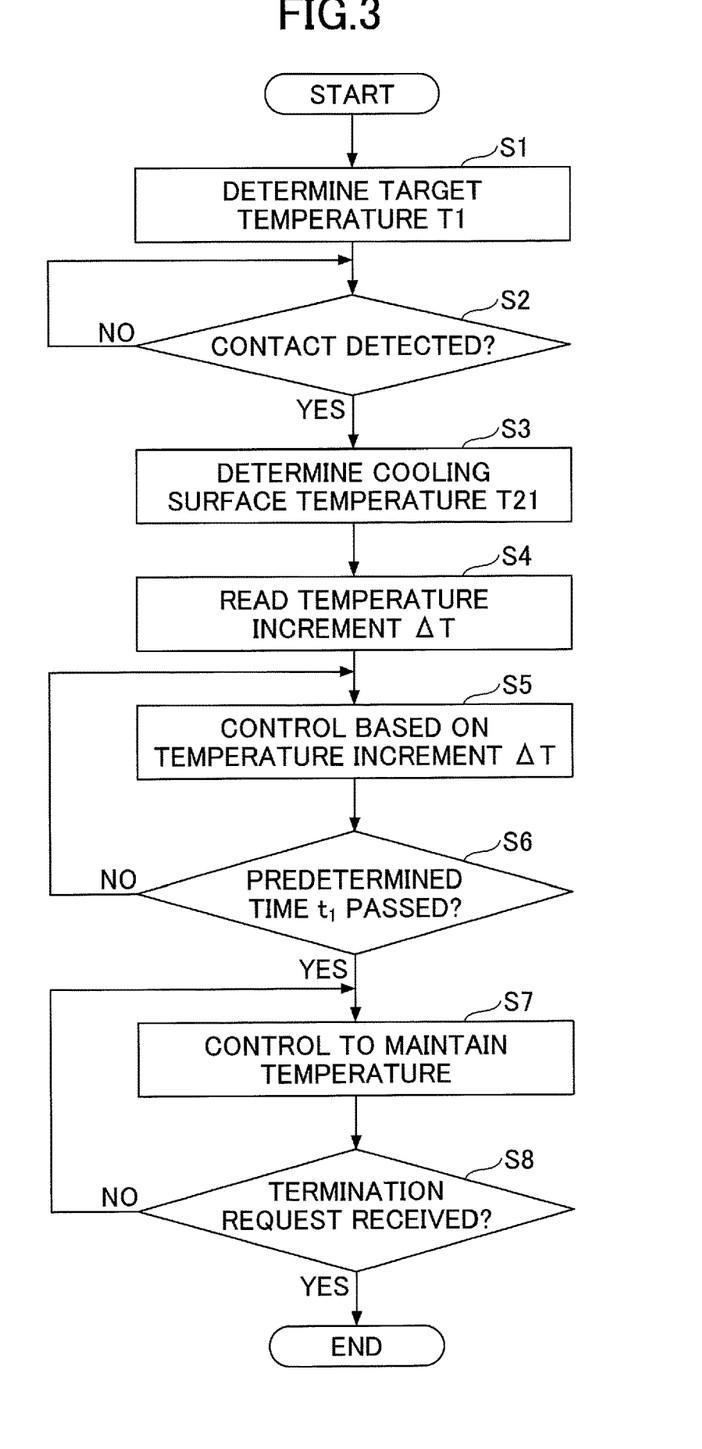
FIG. 3 is a flowchart illustrating a process performed by the controller included in the temperature sensation providing system according to the embodiment.
Figure 4A:
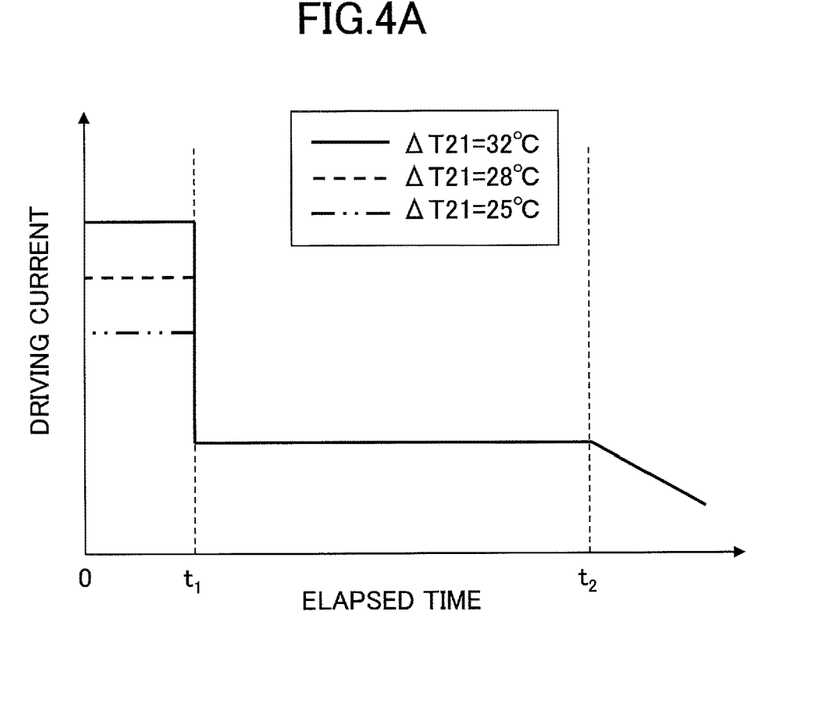
FIGS. 4A and 4B are graphs illustrating an example of a control process performed by a temperature controller included in the temperature sensation providing system according to the embodiment.
Figure 4B:
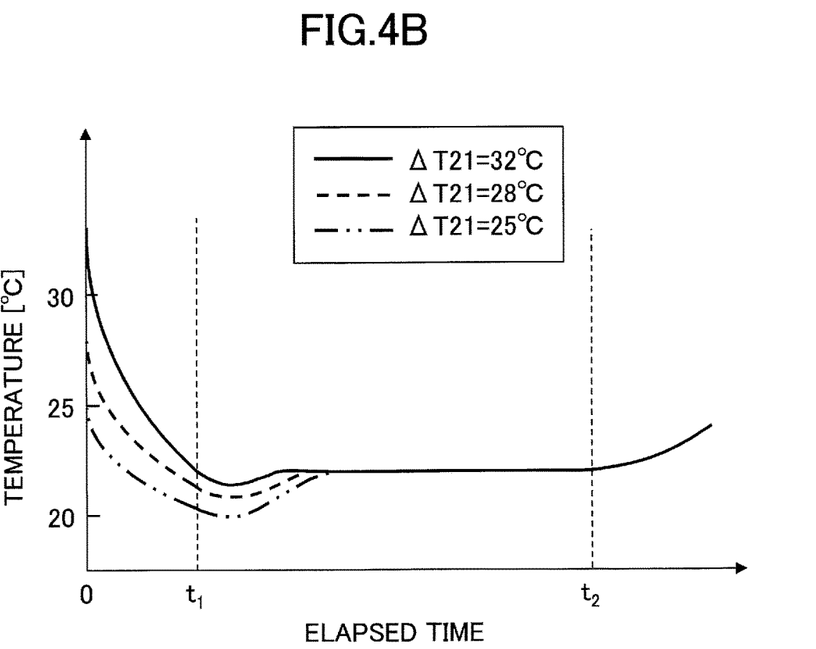

In the present embodiment, the controller 120 performs a control process as described below. FIG. 3 is a flowchart illustrating a process performed by the controller 120. FIGS. 4A and 4B are graphs illustrating an example of a control process performed by the temperature controller 122. FIG. 4A indicates changes in the driving current of the Peltier element 104 being controlled by the temperature controller 122. In FIG. 4A, the vertical axis indicates the driving current, and the horizontal axis indicates elapsed time. FIG. 4B indicates changes in the temperature of the cooling surface of the Peltier element 104 according to changes in the driving current of the Peltier element 104. In FIG. 4B, the vertical axis indicates the temperature, and the horizontal axis indicates elapsed time. In the examples of FIGS. 4A and 4B, it is assumed that the target temperature T1 is 22° C. for all three cooling surface temperatures T21 (32° C., 28° C., and 25° C.).

First, the input unit 121 determines the target temperature T1 at which a temperature sensation is provided by the temperature sensation providing apparatus 100 (step S1). In this example, as described above, the target temperature T1 is 22° C.

Next, the temperature controller 122 determines, via the contact sensor 109, whether the finger 12 is in contact with the Peltier element 104 (step S2). If the finger 12 is in contact with the Peltier element 104, the thermometer 110 measures the cooling surface temperature T21 of the Peltier element 104, and the controller 120 determines the cooling surface temperature T21 (step S3).

Then, the temperature controller 122 reads a temperature increment $\Delta T$ corresponding to the target temperature T1 and the cooling surface temperature T21 from the database 123 (step S4).

Next, the temperature controller 122 controls the temperature of the temperature sensation providing apparatus 100 based on the temperature increment $\Delta T$ (step S5). As described above, in the control information included in the database 123, the deviation of the temperature increment $\Delta T$ at the predetermined time t1 from the actual temperature difference $\Delta T_0$ tends to become greater as the absolute value ($|\Delta T_0|$) of the actual temperature difference $\Delta T_0$ becomes smaller. Accordingly, in the example of FIG. 4A, the driving current is increased as the actual temperature difference $\Delta T_0$ becomes greater (as the cooling surface temperature T21 becomes higher). Also, as indicated in FIG. 4B, the driving current is adjusted such that the reached temperature T22 at a time when the predetermined time t1 passes becomes lower as the absolute value of the actual temperature difference $\Delta T_0$ becomes smaller.

When the predetermined time t1 passes (step S6), for example, as illustrated in FIG. 4A, the temperature controller 122 outputs a constant control signal to the driver circuit 106 regardless of the cooling surface temperature T21 before the start of the control process, and the driver circuit 106 supplies a constant driving current to the Peltier element 104 (step S7). As a result, the temperature of the cooling surface of the Peltier element 104 comes close to the target temperature T1 of 22° C. The database 123 may also include controlled variables indicating the control signal and the driving current after the predetermined time t1.

When a termination request to stop providing the temperature sensation is input at a time t2 (step S8), as illustrated in FIG. 4A, the temperature controller 122 gradually lowers the driving current and terminates the temperature control. As a result, as illustrated in FIG. 4B, the temperature gradually returns to the environmental temperature at the start of the control process.

As described above, the controller 120 of the present embodiment controls the Peltier element 104 based on the control information where cooling surface temperatures T21 of the cooling surface in contact with the finger 12 are associated with temperature increments $\Delta T$ at the predetermined time t1 for each of target temperatures T1. As illustrated in FIG. 4B, this configuration makes it possible to appropriately provide a temperature sensation even when the actual temperature difference $\Delta T_0$ is small. That is, even in a case where an actual temperature difference $\Delta T_0$ is small and a temperature sensation provided by the related-art temperature sensation providing apparatus is likely to be influenced by the environmental temperature, the temperature sensation providing system 10 of the present embodiment can reduce the influence of the environmental temperature.

If the target temperature T1 to be provided and the cooling surface temperature T21 measured by the thermometer 110 are not included in the control information, the target temperature T1 and the cooling surface temperature T21 may be calculated by interpolating or extrapolating a target temperature T1 and a cooling surface temperature T21 included in the control information.

Before the finger 12 contacts the Peltier element 104, the cooling surface of the Peltier element 104 may be kept at a constant temperature such as 32° C. by using the heater 111. This configuration makes it possible to make the cooling surface temperature T21 of the cooling surface in contact with the finger 12 more stable and enables the temperature sensation providing system 10 to operate more stably.

Also, the cooling surface of the Peltier element 104 may be heated to a predetermined temperature such as 32° C. by using the heater 111 when the finger 12 contacts the Peltier element 104, and then a temperature control process to provide the target temperature T1 may be performed.

The supply of a driving current to the Peltier element 104 may be started before the finger 12 contacts the Peltier element 104. However, power consumption can be reduced by starting a temperature control process using the detection of the contact of the finger 12 as a trigger.

Also, in the control information, the cooling surface temperature T21 of the cooling surface in contact with the finger 12 may be associated with a time taken to achieve a predetermined temperature increase instead of the temperature increment $\Delta T$ at the predetermined time t1. For example, when the target temperature T1 is 22° C., a cooling surface temperature T21 of 32° C. may be associated with a time of 0.8 seconds taken to achieve a temperature increase of $-10°$ C., and a cooling surface temperature T21 of 28° C. may be associated with a time of 0.3 seconds taken to achieve a temperature increase of $-10°$ C.

<Variation of Temperature Sensation Providing Apparatus>

Figure 5:
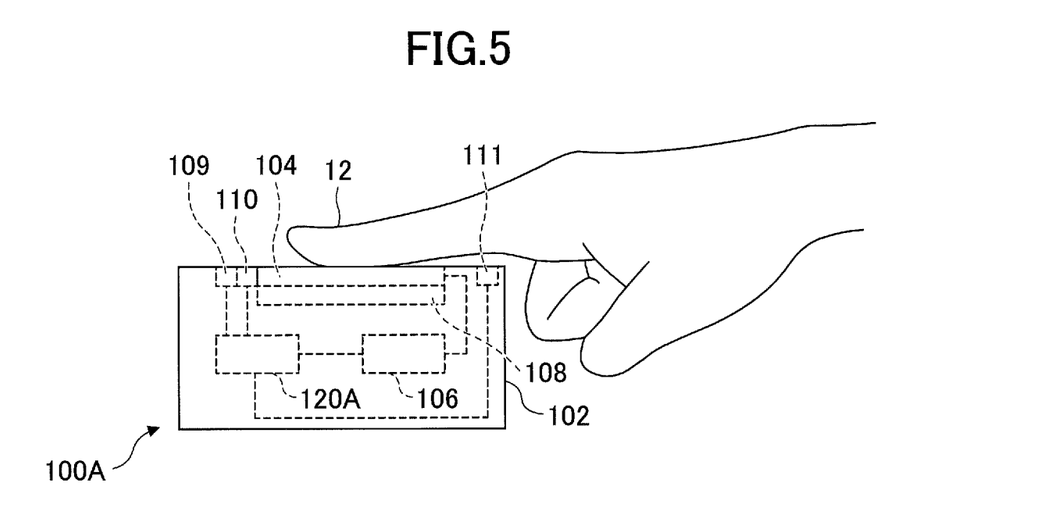
FIG. 5 is a drawing illustrating a temperature sensation providing apparatus according to a variation of the embodiment.

FIG. 5 is a drawing illustrating a variation of the temperature sensation providing apparatus 100. A temperature sensation providing apparatus 100A illustrated in FIG. 5 differs from the temperature sensation providing apparatus 100 in that the temperature sensation providing apparatus 100A includes a controller 120A. The controller 120A includes functions similar to those of the controller 120. Thus, the temperature sensation providing apparatus 100A is configured such that the driving current for driving the Peltier element 104 can be controlled by the controller 120A included in the temperature sensation providing apparatus 100A.

Embodiments of the present invention are described above. However, the present invention is not limited to the specifically disclosed embodiments, and variations and modifications may be made without departing from the scope of the present invention.

For example, in the above embodiment, the present invention is applied to the temperature sensation providing apparatus 100 capable of providing a cold sensation. However, the present invention is not limited to this embodiment, and may also be applied to a temperature sensation providing apparatus capable of providing a warm sensation. Also, for example, the present invention may be applied to a temperature sensation providing apparatus capable of providing both of a cold sensation and a warm sensation. For example, the temperature sensation providing apparatus 100 described above may be configured to provide a warm sensation to the finger 12 of the user contacting a contact surface (heating surface) of the Peltier element 104 by supplying an electric current to the Peltier element 104 in a direction opposite the direction in which an electric current is supplied to provide a cold sensation and thereby generating heat on the contact surface. Also in this case, the influence of the environmental temperature can be reduced by using control information where contact surface temperatures of a contact surface in contact with a finger are associated with temperature increments at a predetermined time for each target temperature. Table 2 below indicates an example of control information.

TABLE 2

| Target Temperature T1 | Heating Surface Temperature T31 | $\Delta T_0$ (=T1-T31) | Temperature increment $\Delta T$ | Reached Temperature T32 |
|---|---|---|---|---|
| 40° C. | 32° C. | +8° C. | +10° C. | 42° C. |
| | 28° C. | +12° C. | +13° C. | 41° C. |
| | 25° C. | +15° C. | +15° C. | 40° C. |
| 42° C. | 32° C. | +10° C. | +12° C. | 44° C. |
| | 28° C. | +14° C. | +15° C. | 43° C. |
| | 25° C. | +17° C. | +17° C. | 42° C. |

In the example of Table 2, for each target temperature T1, heating surface temperatures T31 of the heating surface in contact with the finger 12 are associated with temperature increments $\Delta T$ at the predetermined time t1. In the example of Table 2, for the target temperature T1 of 40° C., the heating surface temperature T31 of 32° C. is associated with the temperature increment $\Delta T$ of +10° C., the heating surface temperature T31 of 28° C. is associated with the temperature increment $\Delta T$ of +13° C., and the heating surface temperature T31 of 25° C. is associated with the temperature increment $\Delta T$ of +15° C. That is, when the heating surface temperature T31 is 32° C., the actual temperature, difference $\Delta T_0$ (=T1−T31) between the target temperature T1 and the heating surface temperature T31 is +8° C., but the temperature increment $\Delta T$ is +10° C. When the heating surface temperature T31 is 28° C., the actual temperature difference $\Delta T_0$ is +12° C., but the temperature increment $\Delta T$ is +13° C. When the heating surface temperature T31 is 25° C., the actual temperature difference $\Delta T_0$ is +15° C., and the temperature increment $\Delta T$ is also +15° C.

Thus, the control information is configured such that as the absolute value ($|\Delta T_0|$) of the actual temperature difference $\Delta T_0$ between the heating surface temperature T31 and the target temperature T1 becomes smaller, the temperature increment $\Delta T$ associated with the heating surface temperature T31 as a controlled variable deviates further from the actual temperature difference $\Delta T_0$. That is, in the control information, the deviation of the temperature increment $\Delta T$ at the predetermined time t1 from the actual temperature difference $\Delta T_0$ tends to increase as the absolute value ($|\Delta T_0|$) of the actual temperature difference $\Delta T_0$ becomes smaller. This tendency need not be present in all actual temperature differences $\Delta T_0$, and is preferably present in the absolute values ($|\Delta T_0|$) of actual temperature differences $\Delta T_0$ that are less than or equal to a given value and at which the user tends to become insensitive. For the target temperature T1 of 42° C., heating surface temperatures T31 are associated with temperature increments $\Delta T$ in a similar manner.

In a control process based on the control information described above, the driving current is increased as the actual temperature difference $\Delta T_0$ becomes greater (as the heating surface temperature T31 becomes lower), and the driving current is adjusted such that the reached temperature T32 at a time when the predetermined time t1 passes becomes higher as the absolute value of the actual temperature difference $\Delta T_0$ becomes smaller.

Also, in the above-described embodiment, after a cold sensation is provided, temperatures in a range between a cooling temperature and an initial skin temperature may be presented. Providing such temperature sensations makes it possible to give the user an illusion of moving a finger away from an object.

In the above embodiment, the present invention is applied to the temperature sensation providing apparatus 100 including the Peltier element 104. However, the present invention is not limited to this embodiment, and may also be applied to a temperature sensation providing apparatus including the Peltier element 104 (or another type of temperature sensation provider) and a tactile sensation provider (e.g., a vibration generator).

An aspect of this disclosure makes it possible to provide a controller, a temperature sensation providing apparatus, a temperature sensation providing system, a control method, and a storage medium that are less susceptible to environmental temperatures.

What is claimed is:

1. A controller for controlling a temperature sensation provider that provides temperature sensations to an object contacting a contact surface of the temperature sensation provider, the controller comprising
    a database including control information that associates values of a temperature of the contact surface with values of a controlled variable of the temperature sensation provider to achieve a temperature increment for each of the temperature sensations such that a deviation between an actual temperature difference and the temperature increment increases as an absolute value of the actual temperature difference decreases, said actual temperature difference being defined by a difference between the temperature of the contact surface and a target temperature for each of the temperature sensations, said temperature increment being defined by a difference between the temperature of the contact surface and a temperature that is measured when a predetermined time elapses after the controller starts to control the temperature sensation provider; and
    a temperature controller that controls the temperature sensation provider based on the temperature of the contact surface, the target temperature for each of the temperature sensations, and the control information.

2. The controller as claimed in claim 1, wherein the control information further includes driving currents that are associated with the values of the controlled variable and to be supplied to the temperature sensation provider.

3. The controller as claimed in claim 1, wherein the control information is configured such that as an absolute value of a first temperature difference between the temperature of the contact surface and the target temperature corresponding to the temperature sensation to be provided becomes smaller, a second temperature difference associated with the temperature of the contact surface as the controlled variable deviates further from the first temperature difference.

4. A temperature sensation providing apparatus, comprising:
    the controller of claim 1;
    the temperature sensation provider that is controlled by the controller; and
    a thermometer that measures the temperature of the contact surface.

5. The temperature sensation providing apparatus as claimed in claim 4, further comprising:
    a heater that heats the contact surface.

6. The temperature sensation providing apparatus as claimed in claim 4, further comprising:
    a contact sensor that detects contact of the object with the temperature sensation provider,
    wherein the temperature controller starts providing the temperature sensation in response to the detection of the contact of the object by the contact sensor.

7. The temperature sensation providing apparatus as claimed in claim 6, wherein the contact sensor is an electrostatic sensor.

8. The temperature sensation providing apparatus as claimed in claim 6, wherein the contact sensor is a temperature sensor.

9. A temperature sensation providing system, comprising:
    the controller of claim 1,
    a temperature sensation providing apparatus including the temperature sensation provider that is controlled by the controller; and
    a thermometer that measures the temperature of the contact surface.

10. A method for controlling a temperature sensation provider that provides temperature sensations to an object contacting a contact surface of the temperature sensation provider, the method comprising:
    referring to a database including control information that associates values of a temperature of the contact surface with values of a controlled variable of the temperature sensation provider to achieve a temperature increment for each of the temperature sensations such that a deviation between an actual temperature difference and the temperature increment increases as an absolute value of the actual temperature difference decreases, said actual temperature difference being defined by a difference between the temperature of the contact surface and a target temperature for each of the temperature sensations, said temperature increment being defined by a difference between the temperature of the contact surface and a temperature that is measured when a predetermined time elapses after the controller starts to control the temperature sensation provider; and
    controlling the temperature sensation provider based on the temperature of the contact surface, the target temperature for each of the temperature sensations, and the control information.

11. A non-transitory computer-readable storage medium that stores a program for causing a computer to execute a process for controlling a temperature sensation provider that provides temperature sensations to an object contacting a contact surface of the temperature sensation provider, the process comprising:
    referring to a database including control information that associates values of a temperature of the contact surface with values of a controlled variable of the temperature sensation provider to achieve a temperature increment for each of the temperature sensations such that a deviation between an actual temperature difference and the temperature increment increases as an absolute value of the actual temperature difference decreases, said actual temperature difference being defined by a difference between the temperature of the contact surface and a target temperature for each of the temperature sensations, said temperature increment being defined by a difference between the temperature of the contact surface and a temperature that is measured when a predetermined time elapses after the controller starts to control the temperature sensation provider; and controlling the temperature sensation provider based on the temperature of the contact surface, the target temperature for each of the temperature sensations, and the control information.

12. The controller as claimed in claim 1, wherein the controller is configured to control the temperature sensation provider only for the predetermined time.

13. The controller as claimed in claim 1, wherein the controller is configured to control the temperature sensation provider only when the absolute value of the difference of the target temperature and the temperature of the contact surface is equal or less than a predetermined value.

\* \* \* \* \*